United States Patent
Niizato et al.

[11] 4,122,171
[45] Oct. 24, 1978

[54] AGENT FOR PROTECTING AGAINST RENAL FAILURE

[75] Inventors: Tetsutaro Niizato; Takashi Tsuruoka, both of Kawasaki; Shigeharu Inouye, Yokohama; Takemi Koeda, Yokohama; Taro Niida, Yokohama, all of Japan

[73] Assignee: Meiji Seika Kaisha, Ltd., Tokyo, Japan

[21] Appl. No.: 786,468

[22] Filed: Apr. 11, 1977

[30] Foreign Application Priority Data

Apr. 16, 1976 [JP] Japan .................................. 51-42380

[51] Int. Cl.$^2$ ........................ A61K 31/70; A61K 31/71
[52] U.S. Cl. ........................................ 424/180; 424/181
[58] Field of Search .................................. 424/180, 181

[56] References Cited

U.S. PATENT DOCUMENTS 3,962,429  6/1976  Furuno et al. .................. 424/181

OTHER PUBLICATIONS

Chemical Abstracts 77: 122650x (1972).

*Primary Examiner*—Jerome D. Goldberg
*Attorney, Agent, or Firm*—Haight & Huard

[57] ABSTRACT

D-glucaro-1,5-lactam and its pharmaceutically acceptable salts are useful as an agent of protecting against renal failure or damage induced by administration of aminoglycosidic antibiotics.

8 Claims, No Drawings

AGENT FOR PROTECTING AGAINST RENAL FAILURE

BACKGROUND OF THE INVENTION

1. Field of the invention

This invention relates to an agent for protecting against renal failure or insufficiency which comprises as the active ingredient D-glucaro-1,5-lactam or a pharmaceutically acceptable salt thereof. More particularly, this invention relates to a drug for protecting against renal failure or insufficiency induced by a chemotherapeutic agent which is more or less nephrotoxic to the kidney, and especially this invention is directed to a drug for preventing renal failure induced by an aminoglycosidic antibiotic such as the kanamycins and 3',4'-dideoxykanamycin B. This invention further relates to a process for protecting against renal failure or insufficiency in animals or humans which is induced by oral or parenteral administration of aminoglycosidic antibiotic.

2. Description of the prior art

Aminoglycosidic antibiotics such as kanamycin A, kanamycin B, 3',4'-dideoxykanamycin B and gentamicin are widely used as antibacterial agents which are remarkably effective for therapeutic treatment of the infections caused by gram-negative and gram-positive bacteria and acid-fast bacteria. However, it has been stated that administration of aminoglycosidic antibiotic such as neomycins, kanamycins, streptomycin and gentamicin may frequently induce renal failure or insufficiency in humans as a main side-effect. It is known that various indicators of the degree of renal dysfunction become worse as the amount of aminoglycosidic antibiotic given to patients increase. It is also known that precaution must be taken when an aminoglycosidic antibiotic is given to such a patient suffering from renal failure.

To protect against or reduce renal failure or insufficiency induced by aminoglycosidic antibiotics is very beneficial in clinical practice. For instance, the "Journal of Antibiotics" Vol. 29, No. 2, pages 187–194 (February 1976) describes some tests where aceglactone (namely, 2,5-di-O-acetyl-D-glucaro-1,4;3,6-dilactone) and its related compounds such as D-glucaro-1,4;3,6-dilactone, sodium D-glucaro-1,4-lactone and sodium D-glucaro-3,6-lactone are administered to rats in an attempt to prevent against or reduce renal failure induced by aminoglycosidic antibiotics.

SUMMARY OF THE INVENTION

We, the present inventors, have now fortunately discovered that the renal failure or insufficiency induced by administration of heavy doses of aminoglycosidic antibiotics such as the kanamycins, 3',4'-dideoxykanamycin B, gentamicin and neomycin can be prevented or reduced to a significant extent by giving an amount of D-glucaro-1,5-lactam or a salt thereof, in combination with aminoglycosidic antibiotics. D-Glucaro-1,5-lactam is a product readily produced from a known antibiotic, nojirimycin, via D-gluco-1,5-lactam. It has further been found that the activity of D-glucaro-1,5-lactam to prevent or protect against the renal failure is higher than that of the aceglactone, which is one of the most potent amongst the monosaccharides tested and mentioned in the above cited pages of the "Journal of Antibiotics". The concept of this invention is based on the aforesaid findings.

DETAILED DESCRIPTION OF THE INVENTION

According to the first aspect of this invention, therefore, there is provided an agent for protecting against renal failure induced by aminoglycosidic antibiotics, which comprises D-glucaro-1,5-lactam or a pharmaceutically acceptable salt thereof as the active ingredient.

The D-glucaro-1,5-lactam and its salts used as the active ingredient in the agent of this invention may be represented by the following structural formula:

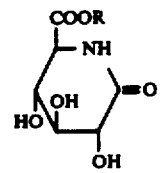

wherein R is a hydrogen atom or a pharmaceutically acceptable metal such as an alkali metal, preferably sodium, potassium, lithium rubidium or cesium, or an alkaline earth metal, preferably magnesium. If desired, the free carboxylic acid form of D-glucaro-1,5-lactam may form an acid-addition salt with kanamycins or 3',4'-dideoxykanamycin B (the free base form) itself.

As D-glucaro-1,5-lactam or an alkali metal or an alkaline earth metal salt thereof is soluble in water, the drug of this invention may be formulated into any orally administable form or a parenterally injectable form known in the art. For instance, the pharmaceutical form for intramuscular, intravenous or subcutaneous injection may be a solution of the active compound in water or a physiological saline solution, and examples of the pharmaceutical form for oral administration may be powders, capsules, tablets, solutions and syrups containing the active compound in admixture with a suitable solid carrier such as talc, calcium carbonate and carbohydrates, e.g. lactose and starch.

It is known that when rats which had been dehydrated by withholding water are given large doses of aminoglycosidic antibiotic by intramuscular injection, such as kanamycin, acute renal failure or damage is regularly induced, and that the renal damage so induced in the dehydrated rats can be enhanced by administration of a blood plasma expander such as dextran, together with the aminoglycosidic antibiotic (see the above cited pages of the "Journal of Antibiotics"). We have also discovered that renal damage can be induced experimentally in rats under normal feeding conditions, when heavier doses of aminoglycosidic antibiotic were continually administered for a certain period. The renal damage may be estimated by observing edema or swelling of the kidney and abnormalities of the renal tubules, epithelial cells of the proximal convoluted tubules and collecting tubule of the kidney, as well as elevation in the level of blood urea nitrogen (hereinafter termed BUN). These changes in the dehydrated rats suffering from acute renal failure induced by an aminoglycosidic antibiotic alone or combined with dextran are very analogous to those involved in human suffering from renal failure induced by administration of aminoglycosidic antibiotics. Accordingly, it is presumed that the administration of aminoglycosidic antibiotic induces renal failure or damage through the common biological mechanism both for the dehydrated rats and human.

We have conducted a series of tests, and we have now found that when D-glucaro-1,5-lactam or a salt thereof which is the active compound used in the agent of this invention is orally or parenterally given to dehydrated rats suffering from acute renal failure caused by intramuscular or intravenous injection of large dose of kanamycin or 3', 4'-dideoxykanamycin B aminoglycosidic antibiotics, alone or combined with dextran, the rise in the level of BUN, the renal edema and pathological abnormalities in the renal tissue can be prevented or reduced to a significant extent owing to the administration of D-glucaro-1,5-lactam or a salt thereof compared to that which would be induced by administration of the aminoglycosidic antibiotic alone without D-glucaro-1,5-lactam. For comparison, we have also tested the known protective effect of aceglactone on renal failure in the same manner as above, and it has been noted that aceglactone is evidently inferior to D-glucaro-1,5-lactam in respect of the protective effect of preventing or reducing renal failure.

In case D-glucaro-1,5-lactam or a metal salt thereof is given orally or parenterally in combination with aminoglycosidic antibiotic, it may be given in a ratio of at least 2 mol., and preferably of 10 mol. or more per 1 mol. of aminoglycosidic antibiotic. In general, the dosage of D-glucaro-1,5-lactam given to provide a beneficial protective effect can be changed depending on the dose of aminoglycosidic antibiotic actually used. For instance, the dosage of 3',4'-dideoxykanamycin B ordinarily administered is totally 100 mg (as the free base form) a day for an adult human in therapeutic treatment of bacterial infections, and therefore the dosage of D-glucaro-1,5-lactam given for achieving a beneficial protective effect may be in a range of 100 mg to 500 mg a day when it is administered in combination with a standard dose of 100 mg/day of 3',4'-dideoxykanamycin B. When D-glucaro-1,5-lactam or a salt thereof as the active compound of this invention is given by parenteral injection, it is most preferred to inject the active compound or the agent of the invention intramuscularly or subcutaneously or intravenously immediately after, simultaneously with or within about 30 minutes before administration of aminoglycosidic antibiotic, as otherwise it would be observed that the intended protective effect of D-glucaro-1,5-lactam is weaker. On the other hand, in cases where D-glucaro-1,5-lactam or a salt thereof as the active compound of this invention is given orally, it is most effective to administer orally D-glucaro-1,5-lactam or a salt thereof within a period of time of from about 5 minutes to about 1 hour before parenteral administration of the aminoglycosidic antibiotic. In cases of intravenous administration, a less toxic metal salt such as the sodium salt is preferable.

In clinical practice, aminoglycosidic antibiotics such as kanamycins, 3',4'-dideoxykanamycin B and gentamicin are usually employed in the form of their acid-addition salt and particularly the sulfate. Although it is, of course, possible to administer the acid-addition salt form of the aminoglycosidic antibiotic, the aminoglycosidic antibiotic can be employed in the form of its free base, in which its basicity can be neutralized by the strong acidity of D-glucaro-1,5-lactam, when the aminoglycosidic antibiotic and D-glucaro-1,5-lactam are given together concurrently. In this case, the free base form of aminoglycosidic antibiotic may constitute an acid-addition salt with D-glucaro-1,5-lactam. For instance, 3',4'-dideoxykanamycin B (the free base) may be combined with D-glucaro-1,5-lactam (the free carboxylic acid form) in a molar ratio of ca. 1:4 in solution in water to give an acid-addition salt of 3',4'-dideoxykanamycin B in which an average of four of the five amino groups of 3',4'-dideoxykanamycin B have each been associated with one molecule of D-glucaro-1,5-lactam. Moreover, the agent of this invention may be in the form of a solution containing a salt of D-glucaro-1,5-lactam together with an acid-addition salt of the aminoglycosidic antibiotic dissolved in water or in physiological saline solution.

Furthermore, it has been found that kanamycins and 3',4'-dideoxykanamycin B given in combination with D-glucaro-1,5-lactam or the salt thereof show substantially no reduction of the antibacterial activity which is inherently shown by these aminoglycosidic antibiotics, and that D-glucaro-1,5-lactam or a metal salt thereof itself causes no renal dysfunction. In order to estimate acute toxicity of salts of D-glucaro-1,5-lactam, the sodium salt and potassium salt of D-glucaro-1,5-lactam were orally given to mice at dosages of 3 g/kg and 5 g/kg, respectively, and it was found that none of the mice so dosed died. This reveals that D-glucaro-1,5-lactam and its salts are the substances of very low toxicity.

As will be clear from the above, the agent of the invention comprising as the active ingredient D-glucaro-1,5-lactam and its salt is useful in that it remarkably protects against renal failure or damage in animals and humans, which would otherwise be induced by administration of aminoglycosidic antibiotic.

According to a second aspect of this invention, therefore, there is provided a process of protecting against renal failure in animals and humans induced by the oral or parenteral administration of an aminoglycosidic antibiotic, which comprises giving to the animal or human orally or parenterally D-glucaro-1,5-lactam or a pharmaceutically acceptable salt thereof at a dosage effective to prevent the renal failure, immediately after, at the same time as or within an appropriate period of time before administration of the aminoglycosidic antibiotic.

The free acid form and sodium salt of D-glucaro-1,5-lactam which are used as the active compound according to this invention are known and may be produced according to the method described in the specification of Japanese Pat. No. 601,999. The potassium salt may be prepared by neutralizing the free acid form of D-glucaro-1,5-lactam with aqueous potassium hydroxide but may also be produced at a low cost by catalytically oxidizing D-gluco-1,5-lactam as a starting material in solution in aqueous potassium hydroxide in the presence of a platinum oxide catalyst, as described in Example 1 below. In this way, the potassium salt of D-glucaro-1,5-lactam may be directly isolated as a crystalline product.

Neutralization of the free acid form of D-glucaro-1,5-lactam with aqueous lithium hydroxide, followed by concentration of the solution and addition of ethanol gives crystalline lithium salt of D-glucaro-1,5-lactam. In a similar way, the rubidium salt, the cesium salt and the magnesium salt of D-glucaro-1,5-lactam can be prepared by using rubidium hydroxide, cesium hydroxide or magnesium hydroxide in place of the lithium hydroxide.

The invention is now illustrated with reference to the following Examples to which the invention is not limited.

EXAMPLE 1

Preparation of D-glucaro-1,5-lactam potassium salt

A solution of 25.6 g of D-gluco-1,5-lactam in 1.22 l. of water was admixed with 60 g of 5% platinum-on-carbon, and the admixture was heated at 55° C. under vigorus agitation, during which time the solution was kept at pH 7.0–8.5 by dropwise addition of 1N aqueous potassium hydroxide. After the reaction was completed the mixture was freed from the catalyst by filtration, the filtrate was concentrated to a volume of about 100 ml., and 40 ml. of methanol was added. After crystal seeds were added, the solution was left to stand at ambient temperature so that potassium salt of D-glucaro-1,5-lactam deposited as the crystals. Yield 29.5 g. mp. 216°–218° C. (with decomposition). $[\alpha]_D^{24}$ + 31.6° (c 1.0%, water).

Elemental analysis

Calculated for $C_6H_8NO_6K \cdot H_2O$ : C 29.06, H 4.07, N 5.65% Found: C 29.28, H 4.05, N 5.53%

The lithium salt of D-glucaro-1,5-lactam similarly prepared showed mp. 275°–278° C. (with decomposition).

Calculated for $C_6H_8NO_6Li$ : C 36.56, H 4.06, N 7.11% Found: C 36.36, H 4.09, N 7.30%

The cesium salt of D-glucaro-1,5-lactam in an amorphous state showed mp. 192°–199° C. (with decomposition).

EXAMPLE 2

Male Wistar SPF rats weighing about 220 g. on an average were fed for 48 hours without water. These dehydrated rats were used as the test animals in three groups each consisting of eight rats. The first group of the dehydrated rats (control) was injected intramuscularly with a solution of 19% (by weight) of kanamycin sulfate in water (0.5 ml.) in a dose of 300 mg base/kg, followed simultaneously by intraperitoneal injection of 10 w/v % aqueous dextran (molecular weight, about 40,000) in a dose of 20 ml./kg. The second group received intramuscular injections of 0.5 ml. of an aqueous solution of 12% (by weight) of D-glucaro-1,5-lactam potassium salt in a dose of 284 mg/kg of the lactam, and the third group received intramuscular injections of 0.5 ml. of an aqueous suspension of 14% (by weight) of aceglactone in a dose of 320 mg/kg of the aceglactone. Immediately after this, the second and third groups so treated were administered kanamycin sulfate and dextran in the same manner and in the same doses as those for the first group (control). The rats of the three groups were then kept in cages under dehydrated conditions with free access to food. 24 Hours after the injection of the antibiotic, the rats were sacrificed by drawing the blood from the inferior vena cava under anesthesia and then the kidneys were excised. The level of BUN in the drawn blood and the weight of kidney edema were measured, and the renal tissue was pathologically examined by microscopic observation. The relative rate of kideny edema was calculated according to the following equation:

$$\text{Kidney edema rate (\%)} = \left(\frac{\text{Kidney weight}}{\text{Body weight}}\right) \times 100$$

The results so obtained are summarized in Table 1 below.

Table 1

| Group | Test Compound | BUN (mg/dl.) | Kidney edema rate (%) | Microscopic observation of kidney tissue |
|---|---|---|---|---|
| 1 | KM+DX (Control) | 124 | 1.39 | Highest abnormality in renal tubule and collecting tubule |
| 2 | KM+DX+GK (Invention) | 39 | 1.09 | Remarkably reduced abnormality in renal tubule & collecting tubule as compared to group 1 |
| 3 | KM+DX+AG (Comparative) | 119 | 1.27 | Higher abnormality in renal tubule & collecting tubule, than that of group 2 |

Notes:
KM denotes kanamycin sulfate, DX dextran, GK D-glucaro-1,5-lactam potassium salt, and AG aceglactone.

EXAMPLE 3

Male Wistar SPF rats weighing 180 g. on an average were dehydrated for 48 hours in the same manner as in Example 2, and these dehydrated rats were used as the test animals in four groups each consisting of eight rats. A first group of the dehydrated rats (group 1, control) was then injected intramuscularly with 0.5 ml. of a solution of 5.1% of 3',4'-dideoxykanamycin B sulfate in water in a dose of 100 mg base/kg, followed simultaneously by intraperitoneal injection of 10 w/v % aquous dextran (molecular weight, about 40,000) in a dose of 20 ml./kg. Three other groups of the dehydrated rats were injected in the same manner as above with the solutions of 3',4'-diedeoxykanamycin B and of dextran, in the same doses immediately after intramuscular injection of either an aqueous solution (0.5 ml.) of 17% (by weight) of potassium salt of D-glucaro-1,5-lactam (Group 2) in a dose of 459 mg/kg of the lactam, or an aqueous solution (0.5 ml.) of 15% (by weight) of sodium salt of D-glucaro-1,5-lactam in a dose of 426 mg/kg of the lactam (Group 3), or an aqueous suspension (0.5 ml.) of 23% (by weight) of aceglactone (Group 4) in a dose of 639 mg/kg of the aceglactone. After injection of the antibiotic, the rats were kept for 24 hours under dehydrated conditions with free access to food, and then sacrificed. The measurement of the BUN level and the kidney edema rate were made in the same way as in Example 2, together with the microscopic observation of the kidney tissue. The results obtained are shown in Table 2 below.

Table 2

| Group | Test Compound | BUN (mg/dl.) | Kidney edema rate (%) | Microscopic observation of kidney tissue |
|---|---|---|---|---|
| 1 | DKB+DX (Control) | 132 | 1.13 | Highest abnormality in renal tubule & collecting tubule |
| 2 | DKB+DX+GK (Invention) | 65 | 0.92 | Remarkable reduction in the induced abnormality, as compared to that of group 1 |
| 3 | DKB+DX+GNa (Invention) | 70 | 0.95 | " |
| 4 | DKB+DX+AG (Comparative) | 126 | 1.07 | Higher abnormality in renal tubule & collecting tubule than those of group |

Table 2-continued

| Group | Test Compound | BUN (mg/dl.) | Kidney edema rate (%) | Microscopic observation of kidney tissue |
|---|---|---|---|---|
| | | | | 2 and 3 |

Notes:
DKB denotes 3',4'-dideoxykanamycin B sulfate and GNa D-glucaro-1,5-lactam sodium salt. DX, GK and AG have the same meanings as given in Table 1.

EXAMPLE 4

Male Wistar rats weighing 266 g. on an average were used without dehydration as the test animals in four groups each consisting of seven rats. The first group was injected intramuscularly with an aqueous solution (0.5 ml.) of 23% (by weight) of 3',4'-dideoxykanamycin B sulfate in a dose of 300 mg base/kg of 3',4'-dideoxykanamycin B. Another two groups were injected in the same manner as above with the same solution of 3',4'-dideoxykanamycin B in the same dose, 5-15 minutes after either intramuscular injection of an aqueous solution (0.5 ml.) of 32% of potassium salt of D-glucaro-1,5-lactam in a dose of 609 mg/kg of the lactam or oral administration of the aqueous solution (1 ml.) of 40% of potassium salt of D-glucaro-1,5-lactam in a dose of 1522 mg/kg of the lactam, respectively. A mixture of powdery 3',4'-dideoxykanamycin B free base and powdery D-glucaro-1,5-lactam in a molar ratio of 1:4 was dissolved in water to a concentration of 45% (by weight) of said mixture, and 0.5 ml. of the resulting aqueous solution of said mixture was intramuscularly injected to the fourth group of rats in a dose of 300 mg base/kg of 3',4'-dideoxykanamycin B and in a dose of 553 mg/kg of D-glucaro-1,5-lactam. The above procedures of administration were repeatedly applied to the above four groups of rats once a day for 3 successive days, respectively. The rats were then kept for 24 hours, after the final injection of the antibiotic, under standard conditions with free access to water and food and subsequently sacrificed. The measurement of the BUN level and the kidney edema rate as well as the microscopic observation of the kidney tissue were made in the same manner as in Example 2. The results so obtained are tabulated in Table 3 below.

Table 3

| Group | Test Compound | BUN (mg/dl.) | Kidney edema rate (%) | Microscopic observation of kidney tissue |
|---|---|---|---|---|
| 1 | DKB (Control) | 139 | 0.97 | Highest abnormality in renal tubule & collecting tubule |
| 2 | DKB+GK (Intramuscularly injected, Invention) | 52 | 0.87 | Remarkable reduction in the induced abnormality, as compared to the injection of DKB alone (group 1) |
| 3 | DKB+GK (Orally administered, Invention) | 49 | 0.83 | " |
| 4 | DKB-GH (Intramuscularly injected, | 60 | 0.90 | " |

Table 3-continued

| Group | Test Compound | BUN (mg/dl.) | Kidney edema rate (%) | Microscopic observation of kidney tissue |
|---|---|---|---|---|
| | Invention) | | | |

Notes:
DKB-GH denotes a mixture of 3',4'-dideoxy-kanamycin B free base with D-glucaro-1,5-lactam in a molar ratio of 1:4. DKB and GH have the same meanings as in the preceeding tables.

EXAMPLE 5

Male Wistar rats dehydrated for 48 hours and weighing 227 g. on an average were used as the test animals in two groups each consisting of the eight dehydrated rats. One group was injected intramuscularly with 0.5 ml. of a solution of 6.5% 3',4'-dideoxykanamycin B sulfate in water in a dose of 100 mg base/kg of 3',4'-diedeoxykanamycin B, followed immediately by intraperitoneal injection of an aqueous solution of 10 w/v % of dextran (molecular weight, ca. 40,000) in a does of 20 ml./kg. A second group of the dehydrated rats was injected in the same manner as above with the solution of 3',4'-dideoxykanamycin B sulfate and of dextran in the same doses, 5-15 minutes after intramuscular injection of 522 mg/kg of D-glucaro-1,5-lactam lithium salt in the form of a solution of 24% of the lithium salt in water. The rats were kept under dehydrated conditions with free access to food. 24 Hours after the injection of the antibiotic, the rats were sacrificed. The measurements of the BUN level in the drawn blood and of the rate of kidney edema were made in the same manner as in Example 2. The results obtained are shown in Table 4 below.

Table 4

| Test Compound | BUN (mg/dl.) | Kidney edema rate (%) |
|---|---|---|
| DKB+DX (Control) | 155 | 1.01 |
| DKB+DX+GLi (Invention) | 65 | 0.84 |

Notes:
GLi denotes D-glucaro-1,5-lactam lithium salt, and DKB and DX have the same meanings as in the preceding tables.

EXAMPLE 6

Male Wistar SPF rats dehydrated for 48 hours and weighing 202 g. on an average were used as the test animals in four groups each consisting of eight rats. A first group of these dehydrated rats was given intramuscularly an aqueous solution of 3.0% (by weight) of neomycin sulfate in a dose of 50 mg base/kg of the neomycin that consisted mainly of neomycin B. The second group of the dehydrated rats was given intramuscularly an aqueous solution of 4.0% (by potency) of gentamicin sulfate in a dose of 100 mg base/kg of the gentamicin that consisted mainly of gentamicin $C_1$, $C_2$ and $C_{1a}$. The third group of the dehydrated rats was injected intramuscularly with the same solution of neomycin sulfate in the same dose as above, 10 minutes after 600 mg/kg of D-glucaro-1,5-lactam potassium salt as an aqueous solution was intramuscularly injected to these rats. The fourth group of the dehydrated rats was injected intramuscularly with the same solution of gentamicin sulfate in the same dose as above, 10 minutes after 600 mg/kg of D-glucaro-1,5-lactam potassium salt as an aqueous solution was injected intramuscularly to these rats. The rats were then kept under dehydrated condition with free access to food. 24 Hours after the injection of the antibiotic, the BUN level in blood was measured. The results so obtained are shown in Table 5 below.

Table 5

| Group | Test Compound (Dose, mg/kg) | BUN (mg/dl.) |
|---|---|---|
| 1 | Neomycin (50) | 87 |
| 3 | Neomycin+GK | 44 |
| 2 | Gentamicin (100) | 50 |
| 4 | Gentamicin+GK | 30 |

EXAMPLE 7

Five groups each consisting of eight Wistar SPF rats weighing 200 g. on an average which had been dehydrated for 48 hours were used as the test animals. The first group of the dehydrated rats was injected intramuscularly with an aqueous solution of 29% (by weight) of kanamycin sulfate in a dose of 500 mg base/kg of the kanamycin. The second group of the dehydrated rats was injected intramuscularly with an aqueous solution of 5.7% (by weight) of 3',4'-dideoxykanamycin B sulfate in a dose of 100 mg base/kg of the 3',4'-dideoxykanamycin B.

The third group of the dehydrated rats was injected intramuscularly with an aqueous solution containing 29% kanamycin sulfate and 24% potassium salt of D-glucaro-1,5-lactam in doses of 500 mg base/kg of the kanamycin and 600 mg/kg of the D-glucaro-1,5-lactam potassium salt. The fourth group of the dehydrated rats was injected intramuscularly with an aqueous solution containing 5.7% 3',4'-dideoxykanamycin B sulfate and 24% potassium salt of D-glucaro-1,5-lactam in doses of 100 mg base/kg of the 3',4'-dideoxykanamycin B and 600 mg/kg of the D-glucaro-1,5-lactam potassium salt. The fifth group of the dehydrated rats was injected intramuscularly with an aqueous solution containing 5.7% 3',4'-dideoxykanamycin B sulfate and 24% lithium salt of D-glucaro-1,5-lactam in doses of 100 mg base/kg of the 3',4'-dideoxykanamycin B and 600 mg/kg of the D-glucaro-1,5-lactam lithium salt.

The rats so treated were kept under dehydrated conditions with free access to food. 24 Hours after the injection of the antibiotics, blood was drawn from these rats and the measurement of the BUN level was made in the same manner as in Example 2. The results obtained are shown in Table 6 below.

Table 6

| Test Compound | BUN (mg/dl.)±standard deviation |
|---|---|
| KM | 94±13.9 |
| DKB | 123±27.7 |
| KM-GK | 50±27.7 |
| DKB-GK | 53±8.9 |
| DKB-GLi | 55±8.5 |

Notes:
KM-GK denotes the mixture of kanamycin sulfate and D-glucaro-1,5-lactam potassium salt; DKB-GK the mixture of 3',4'-dideoxykanamycin B sulfate and D-glucaro-1,5-lactam potassium salt, and DKB-GLi the mixture of 3',4'-dideoxykanamycin B sulfate and D-glucaro-1,5-lactam lithium salt.

EXAMPLE 8

Male Wistar SPF rats dehydrated for 48 hours and weighing 198 g. of an average were used as the test animals in four groups each consisting of eight rats. Each of two groups was given intramuscularly either 0.5 ml. of an aqueous solution of 17% of kanamycin B sulfate in a dose of 300 mg base/kg of the kanamycin B or 0.5 ml. of an aqueous solution of 28% of ribostamycin sulfate in a dose of 500 mg base/kg of the ribostamycin respectively. The remaining two groups of the dehydrated rats were given intramuscularly the same solution of kanamycin B sulfate or the same solution of ribostamycin sulfate in the same doses as above, respectively, 10 minutes after intramuscular injection of 600 mg/kg of D-glucaro-1,5-lactam potassium salts as an aqueous solution of 24% by weight to these rats.

The rats were then kept under dehydrated conditions with free access to food. 24 Hours after the injection of the antibiotic, the BUN level in blood was determined. The results so obtained are shown in Table 7 below.

Table 7

| Group | Test Compound (Dose mg/kg) | BUN (mg/dl.) |
|---|---|---|
| 1 | Kanamycin B (300) | 84 |
| 3 | Kanamycin B+GK | 41 |
| 2 | Ribostamycin (500) | 37 |
| 4 | Ribostamycin+GK | 26 |

EXAMPLE 9

Seven groups each consisting of eight Wistar SPF rats weighing 201 g. on an average were fed commercial rat chow without water for 48 hours, and were used as the test animals. The first group of the dehydrated rats was given intramuscularly an aqueous solution of 5.7% (by weight) of 3',4'-dideoxykanamycin B sulfate in a does of 100 mg base/kg.

Each of the remaining groups of the dehydrated rats was given intramuscularly 3',4'-dideoxykanamycin B sulfate in the same way and in the same dose as those in group 1, 15 minutes after intramuscular administration of an aqueous solution (21%) of D-glucaro-1,5-lactam lithium salt in a dose of 522 mg/kg, an aqueous solution (23%) of D-glucaro-1,5-lactam sodium salt in a dose of 561 mg/kg, an aqueous solution (24%) of D-glucaro-1,5-lactam potassium salt in a dose of 600 mg/kg, an aqueous solution (29%) of D-glucaro-1,5-lactam rubidium salt in a dose of 713 mg/kg, an aqueous solution (33%) of D-glucaro-1,5-lactam cesium salt in a does of 828 mg/kg, and an aqueous solution (21%) of D-glucaro-1,5-lactam magnesium salt in a dose of 535 mg/kg, respectively.

The rats so treated were kept under dehydrated conditions with free access to rat chow. 24 Hours after the injection of the antibiotic, blood was drawn from these rats, and the BUN level was determined in the same manner as in Example 2.

The results obtained are shown in Table 8 below.

Table 8

| Test Compound | Dose of protecting agent (mg/kg) | BUN (mg/dl.) ±standard deviation |
|---|---|---|
| DKB | — | 123±27.7 |
| DKB+GLi | 522 | 69±10.2 |
| DKB+GNa | 561 | 57±12.9 |
| DKB+GK | 600 | 53±9.0 |
| DKB+GRb | 713 | 54±10.1 |
| DKB+GCs | 828 | 50±7.9 |
| DKB+GMg | 535 | 49±9.4 |

Notes:
GRb, GCs, GMg denote the rubidium, cesium and magnesium salt of D-glucaro-1,5-lactam, respectively.

EXAMPLE 10

Seven groups each consisting of ten male Wistar SPF rats weighing 190 g. on an average were fed commercial rat chow without water for 48 hours, and were used as the test animals. The first group of the dehydrated rats was given intramuscularly an aqueous solution of 6.5% (by weight) of 3',4'-dideoxykanamycin B sulfate in a dose of 100 mg base/kg, with concurrent intraperitoneal injection of 10 w/v % aqueous solution of dextran (M.W., ca. 40,000) in a dose of 20 ml./kg.

Each of the second, third and fourth groups of the dehydrated rats was given 3',4'-dideoxykanamycin B sulfate and dextran in the same way and in the same doses as those in group 1, 5-15 minutes after intraperitoneal, subcutaneous and intramuscular injection of 23% solution of D-glucaro-1,5-lactam potassium salt in physiological saline in a dose of 600 mg/kg, respectively.

The fifth group of the dehydrated rats was given intraveneously 2.0% aqueous solution of 3',4'-dideoxykanamycin B sulfate in a dose of 30 mg base/kg. The sixth group of the dehydrated rats was given intravenously a mixed aqueous solution of 3.6% (by weight) of 3',4'-dideoxykanamycin B sulfate in a dose of 30 mg base/kg and D-glucaro-1,5-lactam sodium salt in a dose of 53 mg/kg. The seventh group of the dehydrated rats was given intravenously an aqueous solution of 3.0% (by weight) of a 1:4 (molar) mixture of 3',4'-dideoxykanamycin B and D-glucaro-1,5-lactam in a dose of 30 mg base/kg of the 3',4'-dideoxykanamycin B and 56 mg/kg of D-glucaro-1,5-lactam.

The rats so treated were kept under dehydrated condition with free access to rat chow. 24 Hours after the injection of the antibiotic, or mixtures of the antibiotic and protecting agent, the BUN level in blood was determined in the same manner as in Example 2. The results obtained are shown in Table 9 below.

Table 9

| Group | Test Compound | Administration route | BUN (mg/dl.) |
|---|---|---|---|
| 1 | DKB+DX | intramuscular + intraperitoneal | 158 |
| 2 | DKB+DX+GK | intramuscular + intraperitoneal + intraperitoneal | 65 |
| 3 | DKB+DX+GK | intramuscular + intraperitoneal + subcutaneous | 84 |
| 4 | DKB+DX+GK | intramuscular + intraperitoneal + intramuscular | 67 |
| 5 | DKB | intravenous | 85 |
| 6 | DKB.Gna | intravenous | 40 |
| 7 | DKB.GH | intravenous | 50 |

EXAMPLE 11

A mixture of 3',4'-dideoxykanamycin B and D-glucaro-1,5-lactam in a molar ratio of 1:4 was dissolved in water to prepare an aqueous solution of 3.0% (by weight) of said mixture. This aqueous solution was concentrated to dryness under reduced pressure, affording a white amorphous powder which decomposed at 108°-111° C. This powder was found to be the salt of D-glucaro-1,5-lactam associated with 3',4'-dideoxykanamycin B.

What we claim is:

1. An agent suitable for protecting against renal failure induced by administration of an aminoglycosidic antibiotic, which comprises:
   (a) an effective amount of aminoglycosidic antibiotic selected from the group consisting of kanamycin A, kanamycin B, 3',4'-dideoxykanamycin, gentamycin neomycin, ribostamycin and the pharmaceutically acceptable salts thereof, in association with
   (b) about two to ten moles of D-glucaro-1,5-lactam or a pharmaceutically acceptable acid addition salt thereof per mole of said aminoglycosidic antibiotic.

2. An agent according to claim 1, in association with a pharmaceutically acceptable carrier.

3. An agent according to claim 2, containing about ten moles of (b) per mole of (a).

4. An agent according to claim 1, wherein the free base form of said aminoglycosidic antibiotic is used with said D-glucaro-1,5-lactam.

5. An agent according to claim 4, dissolved in water or in a physiological saline solution.

6. A process for protecting against renal failure induced by the administration of an aminoglycosidic antibiotic selected from the group consisting of kanamycin A, kanamycin B, 3',4'-dideoxykanamycin, gentamycin, neomycin, ribostamycin and the pharmaceutically acceptable salts thereof to humans or animals, which comprises orally or parenterally administering to said human or animal a safe and effective dosage of D-glucaro-1,5-lactam or a pharmaceutically acceptable salt thereof in an amount sufficient to prevent said renal failure immediately after, simultaneously with or within an appropriate period of time before administration of said aminoglycosidic antibiotic.

7. A process according to claim 6, wherein said D-glucaro-1,5-lactam or a salt thereof is orally administered 5 minutes to one hour before administration of said aminoglycosidic antibiotic.

8. A process according to claim 6, wherein said D-glucaro-1,5-lactam or a salt thereof is parenterally administered immediately after or 0-30 minutes before administered of said aminoglycosidic antibiotic.